United States Patent [19]

Kummer

[11] 3,947,503

[45] Mar. 30, 1976

[54] MANUFACTURE OF 1,6-HEXANEDIOL FROM BUTADIENE

[75] Inventor: Rudolf Kummer, Frankenthal, Germany

[73] Assignee: BASF Aktiengesellschaft, Ludwigshafen (Rhine), Germany

[22] Filed: Mar. 7, 1975

[21] Appl. No.: 556,470

[30] Foreign Application Priority Data

Mar. 25, 1974 Germany............................ 2414253

[52] U.S. Cl........ 260/635 E; 260/340.7; 260/615 A
[51] Int. Cl.²......................................... C07C 29/00
[58] Field of Search......... 260/635 E, 635 A, 635 R

[56] References Cited
UNITED STATES PATENTS

| | | | |
|---|---|---|---|
| 2,406,713 | 8/1946 | Senkus............................ | 260/635 E |
| 2,700,685 | 1/1955 | Cooper et al.................. | 260/635 E |
| 2,888,492 | 5/1959 | Fischer et al.................... | 260/635 E |
| 3,383,426 | 5/1968 | Cull et al........................ | 260/635 A |
| 3,404,188 | 10/1968 | Privette et al................ | 260/632 HF |

OTHER PUBLICATIONS

Fell et al., "Tetrahedron Letters", No. 32 (1969), pp. 2721–2723.

*Primary Examiner*—Joseph E. Evans
*Attorney, Agent, or Firm*—Johnston, Keil, Thompson & Shurtleff

[57] ABSTRACT

1,6-Hexanediol is manufactured by hydroformylation of 1,3-butadiene by a process wherein an acetal of pent-3-en-1-al is formed in a first hydroformylation step in the presence of lower alkanols or alkanediols and of rhodium catalysts, and is then converted into 1,6-hexanediol in a second hydroformylation step in the presence of cobalt catalysts, followed by hydrogenation.

3 Claims, No Drawings

MANUFACTURE OF 1,6-HEXANEDIOL FROM BUTADIENE

The invention relates to an improved process for the manufacture of 1,6-hexanediol by hydroformylation of 1,3-butadiene followed by hydrogenation of the hydroformylation products first formed.

Numerous attempts to hydroformylate conjugated dienes have already been made. These showed that if cobalt carbonyl catalysts were used, only one double bond was hydroformylated, and the second double bond was hydrogenated.

A publication in Tetrahedron Letters 32 (1969), page 2721 et seq., discloses that if rhodium catalysts modified with tributylphosphine are used, 1,3-butadiene gives not only monoaldehydes but also dialdehydes, which can be hydrogenated to diols. However, this process suffers from the disadvantage that, of the hydroformylation products obtained in a yield of from 80 to 90%, only about half consists of dialdehydes, and these are predominantly branched. The yield of 1,6-hexanedial or -diol is only about 5%, based on butadiene employed. It is an object of the invention to provide a method of controlling the synthesis of 1,6-hexanediol, based on the hydroformylation of butadiene, so that the yield of 1,6-hexanediol, which is the principal product required, is substantially increased.

I have found that 1,6-hexanediol is obtained advantageously by hydroformylation of 1,3-butadiene by a method wherein, in a first hydroformylation stage, 1,3-butadiene is reacted with carbon monoxide and hydrogen at from 70° to 130°C and from 50 to 600 atmospheres in the presence of rhodium complexes which contain carbon monoxide and tertiary organic phosphines or tertiary organic phosphites and halogen atoms as ligands, and with alkanols or alkanediols of up to 4 carbon atoms, the rhodium compounds are removed and the pent-3-en-1-al-acetal thus obtained is subjected to a second hydroformylation stage, either in the hydroformylation mixture from the first stage or after isolation, with carbon monoxide and hydrogen at from 120° to 220°C and from 20 to 120 atmospheres in the presence of cobalt carbonyl complexes modified with tertiary organic phosphines, and the hydroformylation products thus obtained are hydrogenated in the presence of hydrogenation catalysts at elevated temperatures and superatmospheric pressure and the 1,6-hexanediol is isolated by conventional methods.

The advantage of the process of the invention is that 1,6-hexanediol is obtained from butadiene by a simple method and in good yield. The process is noteworthy since it was unforeseeable that the hydroformylation of the pent-3-en-1-al-acetal, obtained as an intermediate, in the presence of cobalt catalysts would in the main give a straight-chain hydroformylation product. Since the olefinic double bond is not in a terminal position, only the formation of predominantly branched products was to be expected, even in the presence of phosphines as modifiers.

The butadiene used as the starting material does not have to be pure and instead can contain, e.g., up to about 8% of hydrocarbons such as butane or isobutane.

The hydroformylation of 1,3-butadiene, initially involving only one double bond, is effected in the first hydroformylation stage in which carbon monoxide and hydrogen are employed in at least stoichiometric amounts but advantageously in excess, e.g. in an excess of up to 100 mole per cent. The volume ratio of carbon monoxide to hydrogen in the mixture is as a rule from 1:0.25 to 1:4, in particular from 1:1 to 1:2.

The reaction is carried out at from 70° to 130°C, but temperatures from 80° to 120°C have proved particularly suitable. The pressure maintained during the reaction is from 50 to 600 atmospheres, but advantageously from 200 to 400 atmospheres.

The catalysts used for the reaction are rhodium complexes which contain carbon monoxide, tertiary organic phosphines or organic phosphites and halogen atoms as ligands. Suitable halogens are chlorine, bromine or iodine; chlorine and bromine have proved particularly important. An atomic ratio of rhodium to halogen, in the catalyst, of about 1:1 has proved advantageous.

Preferred tertiary organic phosphines or phosphites contain, as organic radicals, at most 2 radicals from amongst identical or different alkyl radicals of 1 to 20 carbon atoms, cycloalkyl radicals of 5 to 12 carbon atoms and mononuclear aralkyl radicals of 7 to 10 carbon atoms, and at least one aryl radical of 6 to 10 carbon atoms. The above radicals may contain substituents which are inert under the reaction conditions, for example one or two hydroxyl groups, alkoxy or carbalkoxy groups of 1 to 4 carbon atoms or halogen atoms bonded to aromatic carbon atoms. Tertiary organic phosphines or organic phosphites in which the organic radicals are at least one phenyl radical which may be substituted by an alkyl group or alkoxy group of 1 to 4 carbon atoms or a chlorine atom, are particularly suitable. The remaining radicals may be identical or different alkyl radicals of up to 20 carbon atoms. Examples of suitable compounds are triphenylphosphine, diethylphenylphosphine, tritolylphosphine, trinaphthylphosphine, diphenylmethylphosphine, diphenylbutylphosphine, tris-p-chlorophenylphosphine, tris-p-carboxymethoxyphenylphosphine, tris-p-cyanophenylphosphine, diphenylphosphonic acid phenyl ester, phenylphosphonic acid diphenyl ester and triphenyl phosphite.

Phosphites and phosphines of which the organic radical is derived from benzene, such as triphenylphosphine, tris-p-chlorophenylphosphine and triphenyl phosphite have proved particularly important for industrial purposes.

Preferred rhodium complexes used as catalysts have the formula $XRhCOL_2$, in which X is chlorine, bromine or iodine, especially chlorine, and L is one of the above phosphines or phosphites.

The reaction can be carried out with complex compounds prepared beforehand, but in industry it is preferred to prepare these in situ. A particularly suitable method has proved to be, e.g., to produce the catalyst in situ under the hydroformylation conditions from one mole of rhodium trichloride and one mole of rhodium trioxide together with excess phosphines or phosphites. The preferred ratio of rhodium to phosphine is from 1:2 to 1:100, in particular from 1:5 to 1:50.

The catalysts are preferably used in amounts from 10 to 100 ppm (calculated as rhodium metal), based on the reaction mixture. Amounts of from 20 to 100 ppm have proved particularly suitable.

The reaction is carried out in the presence of alkanols or alkanediols of up to 4 carbon atoms. Examples of suitable compounds are methanol, ethanol, propanol, butanols, ethylene glycol and 1,2-propanediol or, with a view to the second hydroformylation stage, 1,3- diols such as 1,3-propanediol which form particularly suitable cyclic acetals with the formyl group. The alkanols and alkanediols are employed in amounts which provide at least two hydroxyl groups per formyl group to be introduced, but an excess of from 100 to 1,000 mole per cent has proved suitable.

If the reaction is carried out a priori in the presence of diols, not only cyclic but also polymeric acetals are formed under the reaction conditions. Whilst these can also be decomposed easily, it is frequently advisable first to manufacture acetals of monohydric alcohols, for example the dimethylacetal, and to isolate these acetals and trans-acetalize them by conventional methods with a diol in the presence of strong acid catalysts, such as strongly acid ion exchangers, thereby obtaining almost exclusively the cyclic compounds which are particularly suitable for the second hydroformylation step.

The process is discontinued after one double bond has been hydroformylated. Since the first double bond reacts substantially more rapidly, it is simple to establish experimentally at what time the first hydroformylation stage has been completed.

The reaction mixture thus obtained is preferably distilled so as to recover the catalyst as a residue. This residue can be reused directly for the first hydroformylation stage. If particularly pure end products are to be obtained, it is advisable to isolate the pent-3-en-1-al-acetal from the hydroformylation mixture by distillation. However, it is also possible to remove the catalyst from the reaction mixture, i.e. from the hydroformylation product and the alkanols and alkanediols used, and then subject the mixture directly to the second hydroformylation stage.

In the second hydroformylation stage, the pent-3-en-1-al-acetal obtained in the first stage is hydroformylated with a mixture of carbon monoxide and hydrogen. The composition and the amounts of carbon monoxide and hydrogen correspond to those of the first stage.

In the second stage, the hydroformylation is carried out at from 120° to 220°C, especially from 130° to 200°C, and at from 20 to 120 atmospheres, advantageously from 40 to 90 atmospheres.

The reaction can be carried out in the presence of liquid solvents which are inert under the reaction conditions. Hydrocarbons such as benzene, hexane or naphtha, alkanols or alkanediols which have been used as acetalizing components, and ethers, such as diethyl ether or dibutyl ether, have proved particularly suitable solvents.

The hydroformylation catalyst used for the second stage is a cobalt carbonyl complex modified with tertiary organic phosphines. Though the precise catalyst composition is not known, it is assumed to correspond to the formulae

   ($n = 1$ to 4)

or

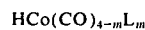   ($m = 1$ to 2)

(L = phosphine).

The concentration of cobalt in the reaction mixture is advantageously from 0.1 to 1 per cent by weight, and preferably from 1 to 10 moles of phosphine are used per gram atom of cobalt. Preferred phosphines are those which are substituted by linear or cyclic alkyl groups of 1 to 20 carbon atoms or phenyl groups which may also contain one or two hydroxyl groups, alkoxy or alkyl radicals of 1 to 4 carbon atoms, carbalkoxy groups of 2 to 5 carbon atoms or halogen atoms. Examples of suitable phosphines are dimethylphenylphosphine, ethylditolylphosphine, trioctylphosphine, tridodecylphosphine, diethyldodecylphosphine and dimethyleicosylphosphine. The phosphorus atom of the trialkylphosphine can also form part of a ring system, as in the case of, e.g., 9-alkyl-9-phosphabicyclononane.

The hydroformylation mixture thus obtained is distilled and separated from the residue containing the catalyst, which can be reused for the same reaction.

The distillate obtained, which consists substantially of 6-hydroxy-hexan-1-al-acetal, is then hydrogenated by conventional methods. Preferred hydrogenation catalysts contain nickel, copper, cobalt, chromium and molybdenum and may be used as unsupported catalysts or on carriers such as aluminum oxide or silica gel. The hydrogenation is advantageously carried out at from 100° to 200°C and from 50 to 300 atmospheres, preferably in the presence of at least stoichiometric amounts of water, based on the acetals contained in the hydroformylation product. 1,6-Hexanediol can easily be obtained in a pure form, from the above reaction mixture, by distillation or crystallization.

1,6-Hexanediol obtained by the process of the invention is an important intermediate for organic syntheses and may be used, e.g., for the manufacture of polyurethanes and polyesters.

EXAMPLE

800 Ml (= 630 g) of methanol, 0.54 g of BrRhCO [P(C$_6$H$_5$)$_3$]$_2$ (= 75 mg of Rh, i.e. 0.72 × 10$^{-3}$ gram atom of Rh) and 10 g of triphenylphosphine (= 39 mmoles) are introduced into a 1 l high pressure vessel. After purging with nitrogen, 200 ml (= 120 g) of butadiene are added and an equimolar mixture of carbon monoxide and hydrogen is then injected until the pressure reaches 200 atmospheres. The mixture is heated to 120°C, whilst raising the pressure to 280 atmospheres. After 40 to 50 minutes, when the gas absorbed is equivalent to a pressure drop of 240 atmospheres, the autoclave is cooled rapidly. The material discharged (839 g) is distilled to free it from the catalyst and traces of residues (15 g total). The product is then subjected to a precision distillation (using a 50 cm packed column), in which excess methanol is first distilled off, followed by the water of acetalization. Finally, penten-3-al-dimethylacetal (163 g, b.p. 57°–62°C/40 mm Hg) and the bis-(dimethylacetals) of the hexanedials (104 g) distil over.

The penten-3-al-dimethylacetal is stirred with 114 g of 1,3-propanediol and 10 g of a strongly acid ion exchanger for 2 hours at 60°C and from 120 to 130 mm Hg, during which the methanol is liberated. The ion exchanger is separated off and the product (193 g) is introduced into a pressure reactor, together with 500 ml of benzene, 3 g (= 8.8 mmoles) of dicobaltoctacarbonyl and 11 g (= 35.5 mmoles) of 9-dodecyl-9-phosphabicyclononane; the vessel is equipped with a magnetic vertically reciprocating stirrer. After twice purging the vessel with a gas mixture of 1 part by volume of carbon monoxide and 2 parts by volume of hydrogen, which is injected until the pressure is 90 atmospheres, the vessel is heated to 170°C and the pressure is maintained at from 80 to 110 atmospheres by further injection of gas. The absorption of gas has ceased after 2 hours and the material discharged is distilled off the catalyst and residue (totaling 18 g). A precision distillation gives 221 g of hydroformylation product which according to analysis by gas chromatography contains only valeraldehyde-acetal, formylvaleraldehydeacetal and hydroxymethylvaleraldehyde-acetal, apart from some 1,3-propanediol.

The hydroformylation product is hydrogenated in the presence of 400 ml of methanol, 100 ml of water and 30 g of Raney nickel at 100°C and 180 atmospheres hydrogen pressure, followed by 140°C and 280 atmospheres hydrogen pressure. The product is subjected to a fractional distillation in which the fractions which pass over are methanol, followed by an azeotrope of amyl alcohol and water, followed, at from 85° to 90°C/1.5 mm, by 1,3-propanediol and finally followed, at from 115° to 120°C/1.5 mm, by 110 g of hexanediols. This corresponds to a yield of 82%, based on the pent-en-3-al-acetal obtained from the first hydroformylation stage. The proportion of 1,6-hexanediol in the total hexanediol isomer mixture is 89 per cent.

If the di-hydroformylation products obtained in the first hydroformylation stage, i.e. the bis(dimethylacetals) of the hexanedials, are also hydrogenated and distilled, a further 53 g of hexanediol mixture is obtained, containing, according to analysis by gas chromatography, 33% of 1,6-hexanediol, 38% of 2-methylpentane-1,5-diol and 39% of 2-ethylbutane-1,4-diol and 2,3-dimethylbutane-1,4-diol.

110 G of pure 1,6-hexanediol are obtained by crystallization from the two hexanediol fractions.

I claim:

1. A process for the manufacture of 1,6-hexanediol by hydroformylation of 1,3-butadiene, wherein, in a first hydroformylation stage, 1,3-butadiene is reacted with carbon monoxide and hydrogen at from 70° to 130°C and from 50 to 600 atmospheres in the presence of a rhodium complex which contains carbon monoxide and a tertiary organic phosphine or tertiary organic phosphite and a halogen atom as ligands, and with an alkanol or alkanediol of 1 to 4 carbon atoms, the rhodium compound is removed, the pent-3-en-1-al-acetal thus obtained is subjected to a second hydroformylation stage, either in the hydroformylation mixture from the first stage after the rhodium compound is removed or after isolation therefrom, with carbon monoxide and hydrogen at from 120° to 220°C and from 20 to 120 atmospheres in the presence of a cobalt carbonyl complex modified with a tertiary organic phosphine, the hydroformylation product thus obtained is hydrogenated by conventional methods in the presence of a hydrogenation catalyst at elevated temperature and superatmospheric pressure, and the 1,6-hexanediol produced is isolated, also by conventional methods.

2. A process as claimed in claim 1, wherein the first hydroformylation stage is carried out in the presence of an alkanol, the resulting pent-3-en-1-al-dialkylacetal is isolated and trans-acetalized with an alkane diol by conventional methods, and the cyclic acetal of the pentenal thus obtained is subjected to the second hydroformylation step.

3. A process as claimed in claim 2, wherein 1,3-propanediol is used as the alkanediol.

* * * * *

UNITED STATES PATENT AND TRADEMARK OFFICE
CERTIFICATE OF CORRECTION

PATENT NO.  : 3,947,503

DATED       : March 30, 1976

INVENTOR(S) : Rudolf Kummer

It is certified that error appears in the above-identified patent and that said Letters Patent are hereby corrected as shown below:

In Column 4, Line 38, delete " 800 Ml " and substitute -- 800 ml --

In Column 4, Line 41, delete " into a 1 l high " and substitute -- into a 2 l high --

Signed and Sealed this

Ninth Day of November 1976

[SEAL]

Attest:

RUTH C. MASON
*Attesting Officer*

C. MARSHALL DANN
*Commissioner of Patents and Trademarks*